United States Patent [19]

Hertl et al.

[11] 4,046,870

[45] Sept. 6, 1977

[54] ASSAY FOR FREE THYROID HORMONES

[75] Inventors: William Hertl, Corning; Gerald Odstrchel, Horseheads, both of N.Y.

[73] Assignee: Corning Glass Works, Corning, N.Y.

[21] Appl. No.: 701,192

[22] Filed: June 30, 1976

[51] Int. Cl.$^2$ .................... G01N 33/00; G01N 33/16
[52] U.S. Cl. .................... 424/1; 23/230 B; 424/12
[58] Field of Search .............. 424/1, 1.5, 12; 23/230 B, 230.6

[56] References Cited

U.S. PATENT DOCUMENTS

| | | | |
|---|---|---|---|
| 3,745,211 | 7/1973 | Brown et al. | 424/1 |
| 3,911,096 | 10/1975 | Chopra | 424/1 |
| 3,928,553 | 12/1975 | Hollander | 424/1 |
| 3,961,894 | 6/1976 | Gordon et al. | 23/230.6 |
| 3,962,039 | 6/1976 | Bates | 195/103.5 R |

*Primary Examiner*—Benjamin R. Padgett
*Assistant Examiner*—Christine M. Nucker
*Attorney, Agent, or Firm*—James A. Giblin; Clinton S. Janes, Jr.; Clarence R. Patty, Jr.

[57] ABSTRACT

Method for determining the concentration of free (unbound) thyroid hormones ($T_3$ or $T_4$) in a fluid sample. The method comprises the steps of performing an immunoassay for total $T_3$ or total $T_4$ in the presence and absence of a blocking agent to establish a binding differential and then correlating that differential with a standard curve which relates known free thyroid hormone concentrations with binding differentials.

7 Claims, 2 Drawing Figures

ASSAY FOR FREE THYROID HORMONES

RELATED APPLICATION

Patent application Ser. No. 701,191, entitled "Assay for Thyroxine-Binding Globulin", filed of even date in the names of W. Hertl and G. Odstrchel and assigned to the present assignee.

BACKGROUND OF THE INVENTION

This disclosure relates generally to the field of immunoassays and specifically to immunoassays used to determine concentrations of thyroxine ($T_4$), triiodothyronine ($T_3$) and thyroxine-binding globulin (TBG) in fluid samples such as blood serum samples.

It is presently throught that the concentration of free $T_4$ ($FT_4$) in a blood serum sample may be more significant clinically than the concentration of total $T_4$ which includes both free (or unbound) $T_4$ and $T_4$ which is bound to serum proteins, especially TBG. Free $T_3$ concentration may also have clinical significance. Since about 99.97% of the $T_4$ (and 99.7% of $T_3$) in normal human serum consists of $T_4$ (or $T_3$) that is bound to serum proteins, one indirect method of measuring either free thyroid hormone (unbound) involves measuring for total thyroid hormone by known means (e.g. immunoassays) and then, by using known binding constants, simply calculating the amount of free $T_4$ (or $T_3$) present. Unfortunately, the use of binding constants to indirectly determine free $T_4$ (or free $T_3$) is not always useful in determining the free thyroid hormones in abnormal human serum. Hence, present methods for determining free $T_4$ or free $T_3$, especially abnormal amounts, are commonly based on an equilibrium dialysis which is a very time consuming method. Quite surprisingly, we have found that either free thyroid hormone can now be rapidly measured by slightly modifying present immunoassay methods for detecting total $T_4$ or total $T_3$. Details of our method are described herein.

SUMMARY OF THE INVENTION

Our method for determining the concentration of free thyroid hormone in a blood serum sample comprises the steps of analyzing the sample via immunoassay technique for either thyroid hormone in the presence and absence of a blocking agent to establish a thyroid hormone binding differential and then correlating that differential with a standard curve relating the respective free thyroid hormone concentrations to binding differentials. In preferred embodiments, the thyroid hormone binding differential is established via solid phase radioimmunoassay (SPRIA) technique (e.g., using anti-$T_4$ or anti-$T_3$ antibodies attached to an insoluble carrier by known means). Preferably, the binding differential is established and represented by the difference between the percent of thyroid hormone bound with and without the blocking agent in a given, fixed, period of time, divided by the percent thyroid hormone bound with the blocking agent. A preferred blocking agent is merthiolate (thimerosal) or ANS (or salt thereof) in an amount sufficient to establish a convenient binding differential. A preferred carrier for the antibodies is silanized glass particles.

SPECIFIC EMBODIMENTS

Figure 2:
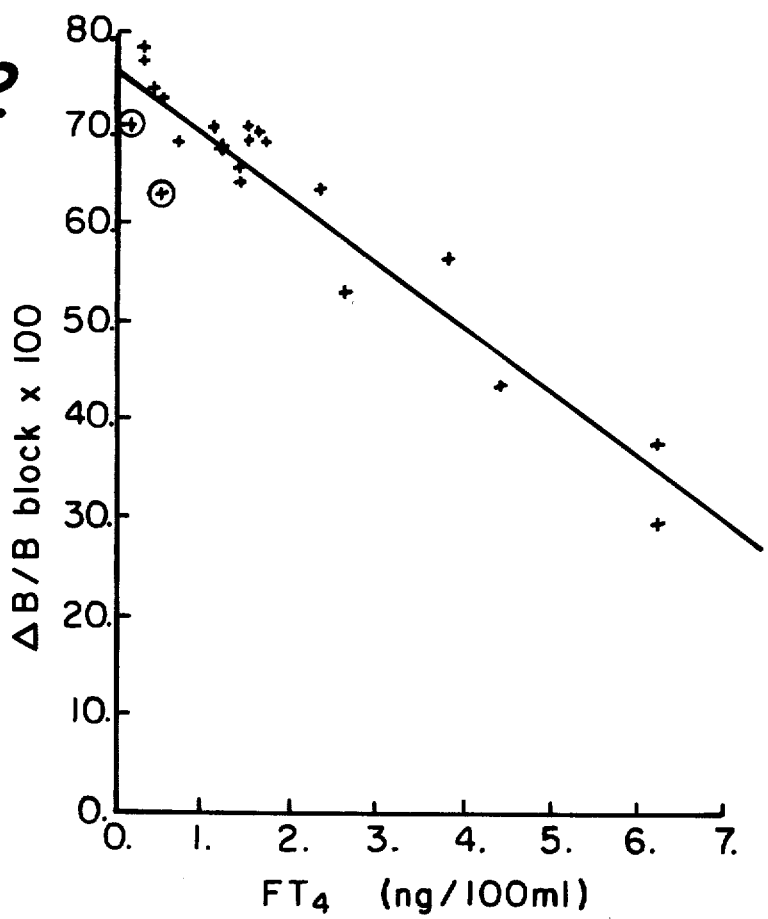
FIG. 2 is another standard curve illustrating a similar linear correlation between free $T_4$ concentrations and corresponding binding differentials established according to the methods disclosed herein.

Very important to our method is the presence and absence of a blocking agent (sometimes called deblocking agent) in an immunoassay for thyroid hormone. Although the disclosed method is especially applicable for determining free $T_4$, it is applicable also for free $T_3$ determinations, since the basic mechanism is similar. Accordingly, as used herein, the expression "thyroid hormone" (T) is deemed to include both $T_3$ and $T_4$ and "free thyroid hormone" (FT) includes both $FT_3$ and $FT_4$. The use of blocking agents in immunoassays for thyroid hormones is described in detail in U.S. Pat. No. 3,911,096 to I. J. Chopra, the teachings of which are incorporated herein by reference. Substances that act as blocking agents include 8-anilino-1-naphthalenesulfonic acid (ANS), merthiolate (thimerosal), dilantin, and many other substances described in the above patent.

Although it is thought that our technique is applicable to all immunoassays (e.g. fluoroimmunoassays, enzyme assisted immunoassays, etc.) the method is especially useful for radioimmunoassays, especially solid phase radioimmunoassays, which are presently being used to measure total $T_4$ or total $T_3$. In the experiments described below, the data was generated using commercially available radioimmunoassay kits for measuring total $T_4$ (i.e. IMMOPHASE $T_4$, Corning Glass Works). It should be stressed, however, that the exact form of the immunoassay "kit" is not critical to our method. Rather, the main requirement is that the immunoassay for $T_3$ or $T_4$ be affected by the use (or non-use) of blocking agents such that a binding differential (e.g. expressed as difference in percent bound) can be established and that a standard curve can be generated using known amounts of free $T_3$ or free $T_4$.

Our method, like that in the related application cited above, resulted from our kinetic studies on the competitive binding reactions of $T_3$ and $T_4$ with their respective immobilized antibodies. We found that the kinetic behavior of $T_3$ and $T_4$ showed many similarities relative to their specific antibodies. From that work, it was observed that the effect of the commonly used blocking agents in those systems (e.g. ANS, merthiolate, etc.) was principally on the rates of the binding reaction to the antibody. The blocking agents are considered generally to displace the $T_3$ or $T_4$ from the serum proteins present in the system. We found that the principal effect of the blocking agent was on the $\alpha$-globulin fraction (TBG) in blood serum. Further, as a result of the kinetic studies, it was found that the rate of the reactions can be described by the following simplified expression:

Rate = $k[FT][IMA]$ where $k$ is a constant, FT is free $T_3$ or free $T_4$, and IMA represents the immobilized antibody used (e.g. anti-$T_3$ or anti-$T_4$ attached, for example, to an insoluble carrier such as silanized glass particles).

The above expression means that the observed rate is proportional to the instantaneous concentration of FT present in the system. Due to the nature of either system, the total $T_3$ or total $T_4$ varies over a wide range and, hence, to obtain a reference value for the total binding which will take place from the total $T_3$ or $T_4$, it is common to concurrently measure the total binding by using a blocking agent as shown, for example in U.S. Pat. No. 3,911,096 to Chopra.

A series of experiments was performed to establish whether the binding differential could be related to free thyroid hormone (FT) levels ranging from low to high clinically significant concentrations. The following data were obtained for a SPRIA $T_4$ system using patient serum samples which had been analyzed for free $T_4$ by means of time consuming equilibrium dialysis. The SPIRA system consisted of anti-$T_4$ antibodies coupled by known means via a silane coupling agent to suspendable glass particles. In one set of experiments to determine % binding of $T_4$, merthiolate blocking agent (also known as thimerosal, $C_9H_9HgNaO_2S$) (2.5 mg/ml) was used as in a commercial $T_4$ RIA kit (Immophase $T_4$ Radioimmunoassay Test System using 125$_I$). In a parallel set of examples, all other conditions were the same except that % binding of $T_4$ was determined without the blocking agent. The difference ($\Delta B$) was then divided by the % binding with the merthiolate (B block) and related to free $T_4$ concentration. The results are shown in Table I.

TABLE I

| Binding Differentials vs. Free $T_4$ Concentration | |
|---|---|
| $\Delta B/B_{block} \times 100$ | Free $T_4$ (ng/100 ml) |
| 77 | 6.2 |
| 68.7 | 1.7 |
| 37.6 | 0.3 |

The values on the right represent, approximately, high, normal, and low values of free $T_4$ found in human serum. Quite fortunately, when the above values of $\Delta B/B_{block}$ are plotted against the values of free $T_4$, a substantially linear plot results. This plot was used as a standard curve and $T_4$ binding rates on further samples were measured, with and without the use of the merthiolate blocking agent. The measured $\Delta B/B_{block}$ values were then entered on the standard curve to obtain the free $T_4$ values. These results were then compared with results (free $T_4$) obtained by the equilibrium dialysis method.

TABLE II

| Differential Results Free $T_4$ (ng/100ml) | Equilibrium Dialysis Results Free $T_4$ (ng/100ml) |
|---|---|
| 5.4 | 4.4 |
| 0.28 | 0.3 |
| 1.50 | 1.6 |
| 7.1 | 6.2 |
| 1.6 | 1.2 |

As indicated, the agreement is satisfactory and it demonstrates that the use of differential rates, as disclosed herein, can be used to obtain concentration values for free thyroid hormone.

Figure 1:
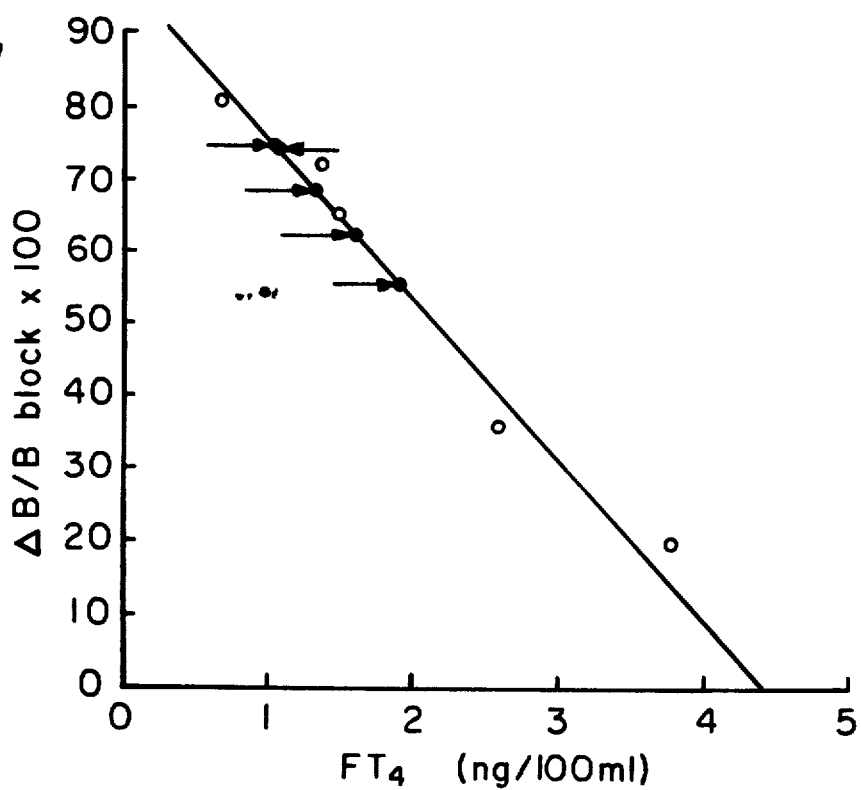
FIG. 1 is a standard curve developed by establishing binding differentials for sera having known $T_4$ concentration as determined via equilibrium dialysis. The arrows indicate binding differential values obtained from male sera known to have $T_4$ values in a normal range (i.e., about 0.8 to 2.2 ng/100 ml).

FIG. 1 is a standard curve covering both sides of the normal range for free $T_4$ concentration. The curve relates differentials ($\Delta B/B_{block} \times 100$) obtained for various known free $T_4$ concentrations. The fine arrows in FIG. 1 indicate that differentials obtained from male sera, known to have a normal $T_4$ value, do fall within the normal range of the curve. The slope of the curve is $-22.2$.

FIG. 2 is another standard curve which also illustrates the general linearity of the relationship of given differentials to known $T_4$ concentrations. The slope of the curve is $-6.64$ and the intercept is 76.1 The correlation of data is 0.90. If the two circled outliers are eliminated, the correlation is 0.94. To generate the curve of FIG. 2, twice as much antibody was used as in generating the curve of FIG. 1. Although this resulted in an increase in range of free $T_4$ measurable, there is a concommitant decrease in sensitivity.

Inasmuch as the method disclosed herein is subject to various modifications, it is intended that the scope of this invention should be limited only by the following claims.

We claim:
1. A method for determining the concentration of free thyroid hormone in a fluid sample, the method comprising the steps of
    1. performing separate immunoassays for thyroid hormone, one immunoassay being in the presence of a blocking agent and the other immunoassay being in the absence of a blocking agent to thereby establish a binding differential; and
    2. then correlating that differential with a standard curve which relates known free thyroid hormone concentrations with binding differentials.

2. The method of claim 1 wherein the immunoassay is a radioimmunoassay.

3. The method of claim 2 wherein the radioimmunoassay is a solid phase radioimmunoassay using composites comprising anti-thyroxine antibodies or anti-triiodothyronine antibodies attached to a water-insoluble carrier.

4. The method of claim 3 wherein the water insoluble carrier comprises silanized glass particles.

5. The method of claim 1 wherein the binding differential is represented by the difference between the percent of thyroid hormone bound with and without blocking agent divided by the percent of thyroid hormone bound with the blocking agent.

6. The method of claim 1 wherein the fluid sample is human blood serum.

7. The method of claim 1 wherein the blocking agent is thimerosal or 8-anilino-1-naphthalensulfonic acid, or a salt thereof.

* * * * *